United States Patent

Mae et al.

[11] Patent Number: 6,156,802
[45] Date of Patent: Dec. 5, 2000

[54] CHOLESTEROL-LOWERING COMPOSITION

[75] Inventors: Tatsumasa Mae, Kakogawa; Takayoshi Hidaka, Kobe, both of Japan

[73] Assignee: Kaneka Corporation, Osaka, Japan

[21] Appl. No.: 09/084,500

[22] Filed: May 27, 1998

[30] Foreign Application Priority Data

May 27, 1997 [JP] Japan .................................. 9-154390

[51] Int. Cl.$^7$ ..................... A61K 31/12; A61K 31/075
[52] U.S. Cl. ..................... 514/690; 514/720; 514/824
[58] Field of Search ..................... 514/690, 720, 514/824

[56] References Cited

U.S. PATENT DOCUMENTS 5,318,993  6/1994  Pearce ..................................... 514/690

FOREIGN PATENT DOCUMENTS 0 659 402 A2  6/1995  European Pat. Off. .
WO98/07417  2/1998  WIPO .

OTHER PUBLICATIONS

XP–00211735, Digiesi et al, Coenzyme Q$_{10}$ in Essential Hypertension, *Molecular Aspects of Medicine*, vol. 15 (Supplement), pp. s257–2263, 1994.
XP–002111736, Shinozawa et al, Protection against Adriamycin (Doxorubicin)–Induced Toxicity in Mice by Several Clnically Used Drugs, *Acta Med. Okayama Univ.*, vol. 41, No. 1, pp. 11–17, 1987.
CA 119:890, Matsura et al., 1993.
CA 124:225417, Lagendijk et al., 1996.
CA 93:230934, Nomura et al., 1980.

*Primary Examiner*—Kimberly Jordan
*Attorney, Agent, or Firm*—Pollock, Vande Sande & Amernick

[57] ABSTRACT

The present invention has its object to provide an antihypercholesterolemic or antihyperlipidemic agent, hence a therapeutic and prophylactic drug for arteriosclerosis, which is safer and more potent in cholesterol-lowering action than the hitherto-available drugs.

A cholesterol-lowering composition comprising a coenzyme Q of the following formula (I) or a reduced coenzyme Q of the following formula (II) as an active ingredient:

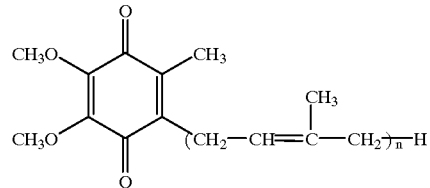

(I)

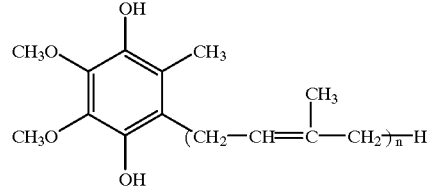

(II)

wherein n represents an integer of 6 to 11

7 Claims, No Drawings

CHOLESTEROL-LOWERING COMPOSITION

FIELD OF THE INVENTION

The present invention relates to a cholesterol-lowering composition comprising a coenzyme Q of the following formula (I) or a reduced coenzyme Q of the following formula (II) as an active ingredient.

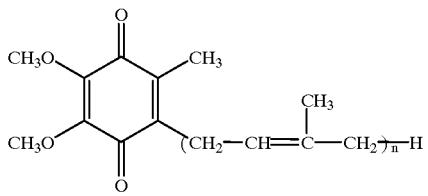

(I)

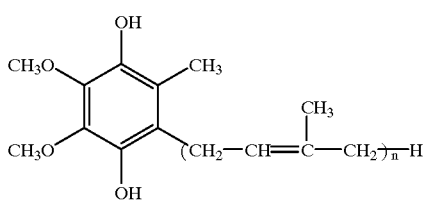

(II)

In the formula n represents an integer of 6 to 11

More particularly, the present invention relates to use of a cholesterol-lowering composition comprising a coenzyme Q of the above formula (I) or a reduced coenzyme Q of the above formula (II) as an active ingredient in the therapy or prophylaxis of hypercholesterolemia, hyperlipidemia, and hence arteriosclerosis.

BACKGROUND ART

With the on-going advance in mean age of the population and changing dietary habit, the number of patients with arteriosclerosis and associated coronary or cerebral arterial disease is on the steady increase. While a number of etiologic factors has been suggested in the onset of arteriosclerosis, elevation of blood cholesterol is regarded as one of chief causative factors and it is being made increasingly clear that for the prevention and treatment of arteriosclerosis, a drug capable of lowering blood cholesterol is effective.

For the pharmacotherapy of hyperlipidemia, available in the main are blood cholesterol-lowering compositions comprising, as active ingredients, fibrates such as clofibrate, simfibrate, clinofibrate, bezafibrate, etc.; nicotinic acid and its derivatives such as nicomol, niceritol, etc.; dextran sulfate; cholestyramine; probucol; 3-hydroxymethylglutaryl (HMG)CoA reductase inhibitors such as pravastatin, simvastatin, lovastatin, etc. [Mizushima, Y. & Miyamoto, A: "Konnichino-Chiryoyaku, Kaisetsu-to-Binran (Therapeutic Drugs Today, Comments and Guides) '97", pp. 419–426, Nankodo]. Among those blood cholesterol-lowering compositions, those comprising cholesterol biosynthesis inhibitors, namely HMG-CoA reductase inhibitors, are clinically highly valued because of their well-defined mechanisms of action and remarkable efficacy.

While those drugs are capable of lowering the blood concentration of cholesterol, they have risks for adverse reactions.

As side effects of fibrates, liver impairment, cholelithiasis, myositis, granuloblastosis, rhabdomyolysis, etc. have been reported.

As typical side effects of nocotinic acid derivatives, facial flush, rash, headache, and vomiting are known.

As side effects of HMG-CoA reductase inhibitors, liver impairment, rhabdomyolysis, elevation of creatine kinase (CPK), diarrhea, abdominal pain, etc. are known.

Even with cholestyramine and probucol, which are comparatively free from side effects, liver impairment and elevation of CPK are known to occur.

Hyperlipidemia in many cases is hyperlipidemia secondary to nephrotic syndrome, obstructive biliary tract disease, hypothrea, or diabetes and many of such patients have diseases other than hyperlipidemia as well. Thus, the recommended therapy for such patients begins with dietetic treatment and ergotherapy, followed by the above drug therapy depending on the time course of serum lipid. If any one drug fails to produce a sufficient response, a combined therapy using a plurality of drugs differing in the mechanism of action is carried out and favorable responses are then obtained in many cases. Thus, a plurality of drugs are used in patients with hyperlipidemia but the risk for drug interactions and potentiation of adverse reactions is increased. For example, the therapy using a fibrate and an HMG-CoA reductase inhibitor may induce rhabdomyolysis and associated acute renal failure.

Meanwhile, cholesterol biosynthesis starts with the synthesis of HMG-CoA from acetyl-CoA and acetoacetyl-CoA and reduction of the HMB-CoA by HMG-CoA reductase to mevalonic acid. Then, starting with mevalonic acid, synthesized are important physiological metabolites such as the cell membrane component sterol; heme A and coenzyme Q, which are involved in electron transport system; dolichol, which is necessary for glycoprotein synthesis; isopentyladenine for transfer RNA; various intracellular signal transporters; and steroid hormones. This process is known as the mevalonic acid pathway [J. L. Goldstein and M. S. Brown, Nature, 343, pp. 425–430, 1990].

Since HMG-CoA reductase mentioned above is a rate-determining enzyme involved in a comparatively early stage of cholesterol biosynthesis, any HMG-CoA reductase inhibitors can be utilized as a cholesterol-lowering agent. However, HMG-CoA reductase inhibitors represented by lovastatin inhibit synthesis of coenzyme Q at the same time [E. L. Appelkvist et al., Clinical Investigator, 71, pp. S97–S102, 1993] and the physiological coenzyme Q level is decreased as a consequence. As a possible cause, it is suspected that the mevalonic acid pathway is shared by coenzyme Q biosynthesis and cholesterol biosynthesis in common.

Japanese Kohai Publication Hei-2-233611 discloses a method comprising using coenzyme $Q_{10}$ in combination with an HMG-CoA reductase inhibitor in order to make up for the decrease in coenzyme $Q_{10}$ caused by an HMG-CoA reductase inhibitor.

A. M. Bargossi et al. report cases in which the combined use of an HMG-CoA reductase inhibitor and coenzyme $Q_{10}$ precluded the decline in coenzyme $Q_{10}$ [Molecular Aspects of Medicine, 15, pp. S187–S193, 1994]. Thus, while simvastatin monotherapy causes not only a fall in blood cholesterol but also a decrease in blood coenzyme $Q_{10}$, the combined therapy with simvastatin and coenzyme $Q_{10}$ may lead to a rise in blood coenzyme $Q_{10}$ without sacrificing the blood cholesterol-lowering effect of simvastatin. However, the dosage of coenzyme $Q_{10}$ in this combined therapy is the dosage required to make up for the decrease in coenzyme $Q_{10}$ without affecting the cholesterol-lowering action of the cardinal drug and is irrelevant to the effective dosage of coenzyme $Q_{10}$, i.e. use of coenzyme $Q_{10}$ as an independent active ingredient.

OBJECT AND SUMMARY OF THE INVENTION

In the view of the above state of the art, the object of the present invention is to provide an antihypercholesterolemic or antihyperlipidemic agent, hence a therapeutic and prophylactic drug for arteriosclerosis, which is safer and more potent in cholesterol-lowering action than the hitherto-available drugs.

After an extensive screening of compounds having cholesterol-lowering activity, the inventors found that a coenzyme Q of the following formula (I) and reduced coenzyme Q of the following formula (II) are highly capable of lowering the blood concentration of cholesterol and have developed the present invention on the basis of the above finding.

The present invention, therefore, is directed to a cholesterol-lowering composition comprising a coenzyme Q of the following formula (I) as an active ingredient:

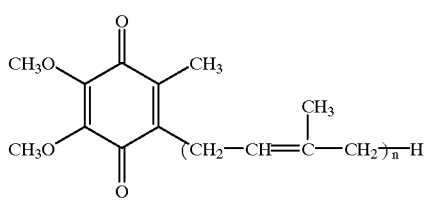

(I)

wherein n represents an integer of 6 to 11

The present invention is also directed to a cholesterol-lowering composition comprising a coenzyme Q of the following formula (II) as an active ingredient:

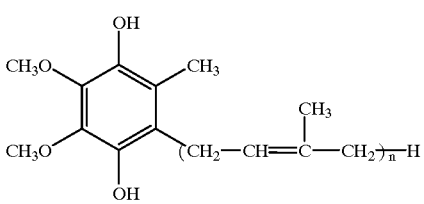

(II)

wherein n represents an integer of 6 to 11

DETAILED DESCRIPTION OF THE INVENTION

The present invention is now described in detail.

The coenzyme Q of the above formula (I) is a class of physiological substances that are involved in electron transport in the mitochondria of living cells and ubiquitous in living things from microorganisms to higher animals.

The reduced coenzyme Q of the above formula (II) is readily transformed to the coenzyme Q of formula (I) in vivo, while this oxidized coenzyme Q is readily transformed to said reduced coenzyme Q in vivo. Therefore, the coenzyme Q in vivo can be generally expressed as follows:

wherein n represents an integer of 6 to 11

It is known that a substantial proportion of physiological coenzyme Q exists in the reduced form, the usual proportion being about 40 to 90%.

Because the coenzyme Q of formula (I) and reduced coenzyme Q of formula (II) have blood cholesterol-lowering activity, a cholesterol-lowering composition comprising said coenzyme Q of formula (I) or reduced coenzyme Q of formula (II) finds application as an antihypercholesterolemic agent, an antihyperlipidemic agent, and hence a therapeutic and prophylactic drug for arteriosclerosis.

Particularly, among species of said coenzyme Q of formula (I) and reduced coenzyme Q of formula (II), coenzyme $Q_{10}$ corresponding to n=10 and reduced coenzyme $Q_{10}$ corresponding to n=10 are coenzymes existing in higher animals inclusive of man and constitute one of the human body components. In human blood, it occurs in its lipoprotein fraction, with reduced coenzyme $Q_{10}$ accounting for no less than 80% of the coenzyme [Kishi, T., Mori, K. Japanese Society of Vitamins (ed.): Vitamin-no-Jiten (Dictionary of Vitamins), pp. 402–413, Asakura Shoten]. Coenzyme $Q_{10}$ has heretofore been used as a therapeutic drug for congestive heart failure, a nutrient, or a nutritional supplement and has proved to be a safe substance. Therefore, it can be used with particular advantage as the active ingredient of the blood cholesterol-lowering composition of the invention.

The reduced coenzyme $Q_{10}$ can also be used with particular advantage as the active ingredient of the composition of the invention.

The above cholesterol-lowering composition can be safely administered orally or otherwise. The dosage form is not particularly restricted but can be freely selected from among powders, tablets, granules, capsules, injections, suppositories, and so on.

In preparing the above cholesterol-lowering composition, other pharmaceutically acceptable components may be mixed appropriately in conventional manners. Such components are not restricted in particular but includes an excipient, disintegrator, lubricant, binder, antioxidant, coloring agent, flocculation inhibitor, absorption promoter, solubilizer, stabilizer, etc.

The excipient mentioned above is not particularly restricted but includes sucrose, lactose, glucose, corn starch, mannitol, crystalline cellulose, calcium phosphate, and calcium sulfate, among others.

The disintegrator includes but is not limited to starch, agar, calcium citrate, clacium carbonate, sodium hydrogencarbonate, dextrin, crystalline cellulose, carboxymethylcellulose, and gum tragacanth.

The lubricant includes but is not limited to talc, magnesium stearate, polyethylene glycol, silica, and hydrogenated vegetable oil.

The binder includes but is not limited to ethylcellulose, methylcellulose, hydroxypropylmethylcellulose, gum tragacanth, shellac, gelatin, gum arabic,

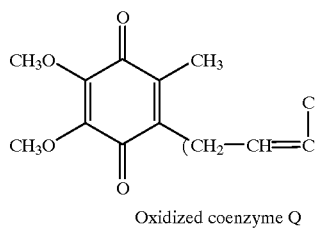

Oxidized coenzyme Q

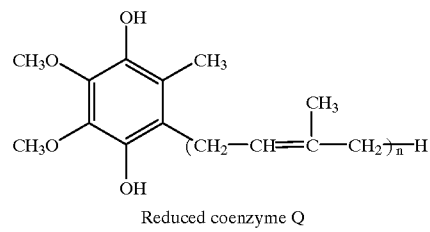

Reduced coenzyme Q polyvinylpyrrolidone, polyvinyl alcohol, polyacrylic acid, polymethacrylic acid, and sorbitol.

The antioxidant includes but is not limited to ascorbic acid, tocopherol, vitamin A, β-carotene, sodium hydrogensulfite, sodium thiosulfate, and sodium pyrosulfite.

The coloring agent is not particularly restricted but a suitable one can be selected from among the colors approved for use in pharmaceutical products.

The flocculation inhibitor includes but is not limited to stearic acid, talc, light silicic acid anhydride, and hydrous silicon dioxide.

The absorption promoter includes but is not limited to higher alcohols; higher fatty acids; and surfactants such as glycerin fatty acid esters.

The solubilizer includes but is not limited to organic acids such as fumaric acid, succinic acid, and malic acid.

The stabilizer includes but is not limited to benzoic acid, sodium benzoate, and ethyl p-hydroxybenzoate.

The cholesterol-lowering composition of the present invention can be administered for the prevention or treatment of hypercholesterolemia or hyperlipidemia. Therefore, the cholesterol-lowering composition of the invention that is an antihypercholesterolemic or antihyperlipidemic agent is also an embodiment of the invention.

The dosage of the above cholesterol-lowering composition depends on the type and severity of hypercholesterolemia or hyperlipidemia but the usual dosage for an adult human is preferably about 100 mg to 10 g per day. Actually, the necessary efficacy is obtained at a higher dose compared with the dosage used in the combined therapy with an HMG-CoA reductase inhibitor.

The cholesterol-lowering composition of the present invention as described in detail above is a safe drug with a low risk for adverse reactions and can be used in the treatment and prevention of hypercholesterolemia, hyperlipidemia, and hence arteriosclerosis.

BEST MODE FOR CARRYING OUT THE INVENTION

The following examples and formulation examples illustrate the present invention in further detail, it being to be understood that those examples are by no means limitative of the scope of the invention.

EXAMPLE 1

Cholesterol-lowering Effect

Male ICR mice weighing about 20 g (5 individuals per group) were put on high cholesterol-cholic acid diet (71.9% standard ration, 15% sucrose, 2% sodium chloride, 10% coconut oil, 0.6% cholesterol, 0.2% cholic acid, 0.3% choline chloride) for feeding ad libitum from day 1 to day 7 of the experiment. On days 6 and 7, reduced coenzyme $Q_{10}$ was administered orally in doses of 150 mg/kg. As a positive control, the commercial antihyperlipidemic bezafibrate was administered orally in doses of 50 mg/kg. After the administration, the mice were deprived of food for 24 hours. On day 8, the blood was drawn from each animal and the serum was separated.

Heparin was added to an aliquot of the serum to cause precipitation and a heparin-precipitated lipoprotein fraction was recovered as low-density lipoprotein (LDL). The serum total cholesterol value and the cholesterol content in LDL were determined by the method described in the report of C. C. Allain et al. [Clinical Chemistry, 20, pp. 470–475, 1974]. The % decreases in serum total cholesterol and LDL cholesterol were calculated by means of the following equation (1), with the corresponding values in the negative control group being respectively taken as 100%.

$$\% \text{ Decrease} = \left(1 - \frac{\text{cholesterol in test group}}{\text{cholesterol in negative control group}}\right) \times 100 \quad (1)$$

The value found by subtracting LDL cholesterol from serum total cholesterol was calculated as high-density lipoprotein (HDL) cholesterol. The percent increase in HDL cholesterol was calculated by means of the following equation (2), with the corresponding value in the negative control group being taken as 100%.

$$\% \text{ Increase} = \left(\frac{\text{cholesterol in test group}}{\text{cholesterol in negative control group}} - 1\right) \times 100 \quad (2)$$

The results are presented in Table 1. It can be seen from Table 1 that reduced coenzyme $Q_{10}$ has a definite property to lower total cholesterol in serum. It is particularly noteworthy that the drug causes a marked decrease in LDL cholesterol which includes cholesterol responsible for deposition of cholesterol on the vascular wall and consequent aggravation of arteriosclerosis and which is known as "risk-factor" cholesterol, and also a marked increase in HDL cholesterol which is said to prevent arteriosclerosis and is known as "antirisk-factor" cholesterol.

Comparison of the commercial antihyperlipidemic bezafibrate used as positive control with reduced coenzyme $Q_{10}$ revealed that although reduced coenzyme $Q_{10}$ was slightly inferior in the action to lower serum total cholesterol, it was somewhat superior in the property to lower LDL cholesterol and very prominent in HDL cholesterol-increasing activity.

It is clear from the foregoing that reduced coenzyme $Q_{10}$ is a highly safe and superior cholesterol-lowering agent.

TABLE 1

|  | Negative control | Reduced coenzyme $Q_{10}$ | Bezafibrate |
| --- | --- | --- | --- |
| Serum total cholesterol (% decrease) | 325 ± 31 mg/dl (0%) | 258 ± 37 mg/dl (21%) | 244 ± 11 mg/dl (25%) |
| LDL cholesterol (% decrease) | 245 ± 33 mg/dl (0%) | 160 ± 39 mg/dl (35%) | 171 ± 16 mg/dl (30%) |
| HDL cholesterol (% increase) | 80 ± 4 mg/dl (0%) | 98 ± 4 mg/dl (23%) | 73 ± 6 mg/dl (−9%) |

Each cholesterol value (mg/dl) is mean ± S. E. (n = 5)

Formulation Example 1

Manufacture of Powders

Powders were manufactured using the following components. Coenzyme $Q_{10}$ was dissolved in acetone, adsorbed on microcrystalline cellulose, followed by drying. The mixture is mixed with corn starch to provide powders containing 20 mg of coenzyme $Q_{10}$ in each 200 mg.

| Coenzyme $Q_{10}$ | 10 parts by weight |
| --- | --- |
| Microcrystalline cellulose | 40 parts by weight |
| Corn starch | 50 parts by weight |

Formulation Example 2

Manufacture of Tablets

Tablets were manufactured using the following components. Coenzyme $Q_{10}$ was dissolved in acetone, and adsorbed on microcrystalline cellulose, followed by drying. Then, corn starch, lactose, carboxymethylcellulose, and magnesium stearate were added and an aqueous solution of polyvinylpyrrolidone was further added as binder. The whole mixture was granulated in conventional manners and after addition of talc as lubricant, the granules were compressed to provide tablets containing 20 mg of coenzyme $Q_{10}$ in each tablet.

| | |
|---|---|
| Coenzyme $Q_{10}$ | 20 parts by weight |
| Microcrystalline cellulose | 4 parts by weight |
| Corn starch | 25 parts by weight |
| Lactose | 15 parts by weight |
| Carboxymethylcellulose | 10 parts by weight |
| Magnesium stearate | 3 parts by weight |
| Polyvinylpyrrolidone | 5 parts by weight |
| Talc | 10 parts by weight |

Formulation Example 3

Manufacture of Capsules

The following components were processed into granules in routine manners and dispensed into hard gelatin capsule shells to provide capsules containing 20 mg of coenzyme $Q_{10}$ per capsule.

| | |
|---|---|
| Coenzyme $Q_{10}$ | 20 parts by weight |
| Microcrystalline cellulose | 40 parts by weight |
| Corn starch | 20 parts by weight |
| Lactose | 62 parts by weight |
| Magnesium stearate | 2 parts by weight |
| Polyvinylpyrrolidone | 3 parts by weight |

Formulation Example 4

Manufacture of Soft Capsules

Soft capsules were manufactured using the following components. Soybean oil was heated to 60° C. and coenzyme $Q_{10}$ melted at 60° C. was added. To this mixture was added vitamin E in small portions and the resulting homogenate was encapsulated to provide soft capsules containing 20 mg of coenzyme $Q_{10}$ in each capsule.

| | |
|---|---|
| Coenzyme $Q_{10}$ | 20 parts by weight |
| Vitamin E | 15 parts by weight |
| Soybean oil | 350 parts by weight |

Formulation Example 5

Manufacture of Powders

Using coenzyme $Q_7$ in lieu of coenzyme $Q_{10}$, the procedure of Formulation Example 2 was otherwise repeated to provide powders.

Formulation Example 6

Manufacture of Tablets

Using coenzyme $Q_9$ in lieu of coenzyme $Q_{10}$, the procedure of Formulation Example 3 was otherwise repeated to provide tablets.

Formulation Example 7

Manufacture of Capsules

Using reduced coenzyme $Q_9$ in lieu of coenzyme $Q_{10}$, the procedure of Formulation Example 4 was otherwise repeated to provide capsules.

Formulation Example 8

Manufacture of Soft Capsules

Using reduced coenzyme $Q_{10}$ in lieu of coenzyme $Q_{10}$, the procedure of Formulation Example 5 was otherwise repeated to provide soft capsules.

What is claimed is:

1. A method for lowering LDL-cholesterol level or elevating HDL-cholesterol level in blood of a mammal or both, which comprises administering an effective amount of a coenzyme Q of the following formula (I):

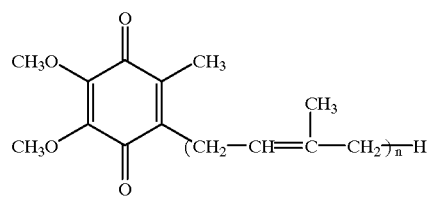

wherein n represents an integer of 6 to 11, or a reduced coenzyme Q of the following formula II:

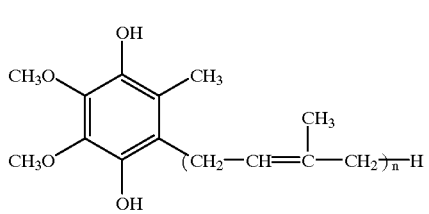

wherein n represents an integer of 6 to 11, or both, to the mammal when the mammal is put on high cholesterol diet.

2. The method according to claim 1, wherein said coenzyme Q is coenzyme $Q_{10}$ wherein n is 10.

3. The method of claim 1 wherein the coenzyme Q is administered at a daily dosage of about 100 mg to 10 g.

4. The method of claim 1 wherein the administering is orally, by injection or by suppository.

5. The method of claim 1 wherein the administering is orally.

6. The method of claim 1 wherein the coenzyme Q is administered along with another pharmaceutically acceptable component.

7. The method of claim 6 wherein the another pharmaceutically acceptable component is selected from the group consisting of excipient, disintegrator, lubricant, binder, antioxidant, coloring agent, flocculation inhibitor, absorption promoter, solubilizer and stabilizer.

* * * * *